(12) United States Patent
Halilah

(10) Patent No.: US 9,435,199 B1
(45) Date of Patent: *Sep. 6, 2016

(54) SELF-CALIBRATING FLUID MEASURING DEVICE

(71) Applicant: Sami O. Halilah, Sugar Land, TX (US)

(72) Inventor: Sami O. Halilah, Sugar Land, TX (US)

(73) Assignee: DYNAMIC FLOW COMPUTERS, INC., Stafford, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,272

(22) Filed: Jul. 30, 2015

(51) Int. Cl.
*G01L 7/00* (2006.01)
*G01F 1/00* (2006.01)
*E21B 49/08* (2006.01)

(52) U.S. Cl.
CPC ............... *E21B 49/087* (2013.01); *G01L 7/00* (2013.01); *G01F 1/00* (2013.01)

(58) Field of Classification Search
CPC . B02C 23/06; B23B 29/046; B23B 31/1074; C04B 2103/52; C04B 24/001; C04B 24/124; G01F 1/40; G01L 19/0007; G01L 19/0092; H05H 1/10; H05H 1/12; H05H 1/14; Y02E 30/126; Y10T 408/957; Y10T 82/02
USPC .................................................. 73/756, 861
See application file for complete search history.

(56) References Cited

U.S. PATENT DOCUMENTS

| | | | |
|---|---|---|---|
| 4,637,756 A | 1/1987 | Boles | |
| 4,638,672 A | 1/1987 | McCall | |
| 4,703,664 A | 11/1987 | Kirkpatrick et al. | |
| 4,753,111 A | 6/1988 | Caron et al. | |
| 4,812,049 A | 3/1989 | McCall | |
| 5,363,699 A * | 11/1994 | McCall | F15D 1/02 138/37 |
| 5,571,970 A | 11/1996 | Mutoh et al. | |
| 5,814,738 A | 9/1998 | Pinkerton et al. | |
| 7,500,405 B2 | 3/2009 | McCall et al. | |
| 8,201,457 B1 * | 6/2012 | Halilah | G01F 1/40 73/756 |
| 2002/0100316 A1 | 8/2002 | James et al. | |
| 2011/0138929 A1 * | 6/2011 | Young | G01F 1/40 73/861.42 |

* cited by examiner

Primary Examiner — John Fitzgerald
Assistant Examiner — Gedeon M Kidanu
(74) Attorney, Agent, or Firm — Buskop Law Group, PC; Wendy Buskop

(57) ABSTRACT

A self-calibrating fluid measuring device for calculating density and velocity of a fluid. The device can have a hollow body with a chamber for receiving and emitting fluid, a ledge, a conical section mount positioned in the hollow body and secured to the ledge, a temperature sensor extending into a temperature port and an upstream static pressure sensor mounted in a static upstream pressure port, a downstream cone pressure drop sensor mounted in a downstream pressure port, and a ram velocity sensor mounted in a ram velocity port, which can all extend into the chamber. A detachable and re-attachable conical area ratio changer can be connected to the conical section mount having a central bore and a hollow fastener configured to align and center the detachable and re-attachable conical area ratio changer to the conical section mount during measurement.

18 Claims, 8 Drawing Sheets

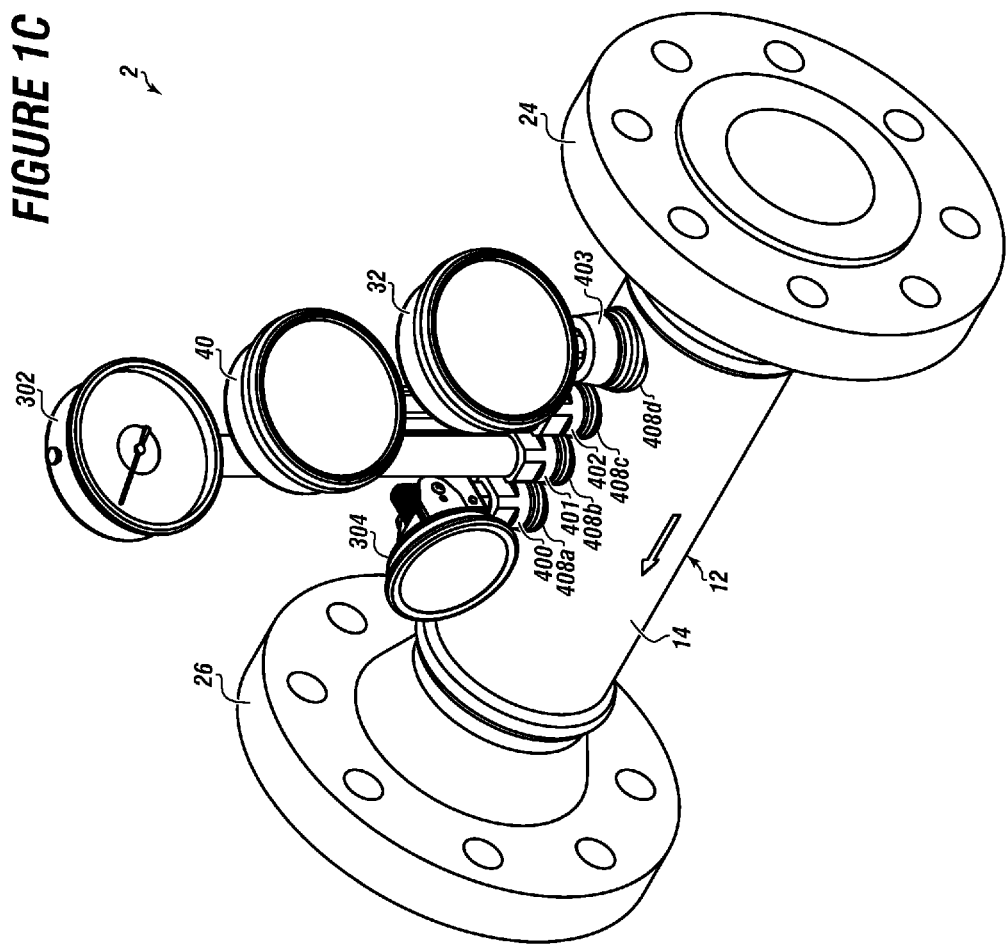

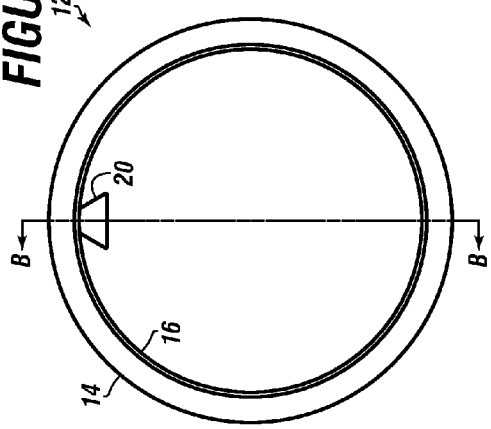
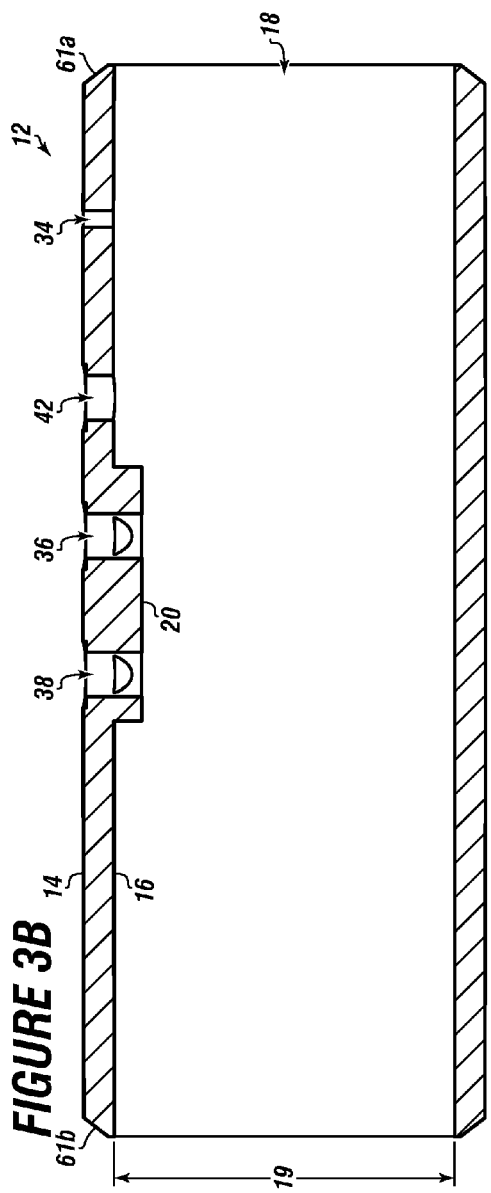

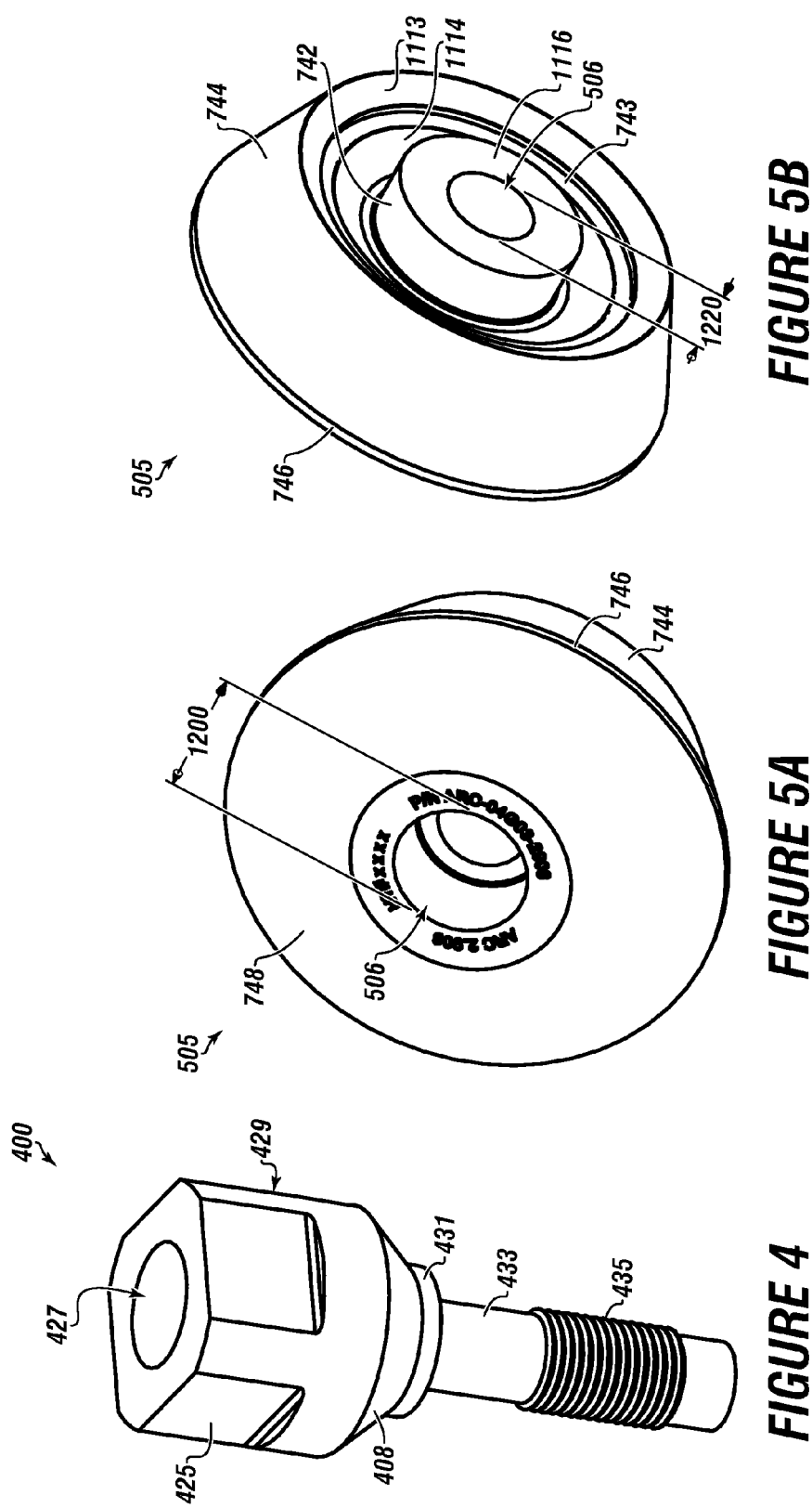

SELF-CALIBRATING FLUID MEASURING DEVICE

FIELD

The present embodiments generally relate to a self-calibrating fluid measuring device that can measure velocity and density.

BACKGROUND

A need exists for a rugged and reliable fluid measuring device to measure accurately and continuously flowing density of fluid samples for fluids coming from a wellbore.

A need exists for a fluid measuring device to continuously measure volume of fluid samples for fluids coming from a pipeline.

A need exists for a fluid measuring device with a conical section mount that is self-centered and self-aligned.

A need exists for a fluid measuring device with a detachable and re-attachable area ratio changer allowing for replacement and maintenance without affecting the alignment of the conical section mount within the hollow body.

A need exists for a fluid measuring device that has a temperature port for recording temperature at an optimal location proximate the pressure measurement ports without disrupting fluid flow.

The present embodiments meet these needs.

BRIEF DESCRIPTION OF THE DRAWINGS

The detailed description will be better understood in conjunction with the accompanying drawings as follows:

FIG. 1C is an assembled view of the self-calibrating fluid measuring device of FIG. 1A.

FIG. 3A is a cross sectional view of the hollow body of the self-calibrating fluid measuring device.

FIG. 3B is a view of the hollow body along the cut lines B-B shown in FIG. 3A.

FIG. 4 is a perspective view of a tab of the plurality of tabs with a bore for receiving a sensor usable in the hollow body.

FIG. 5A depicts a front perspective view of the detachable and re-attachable conical area ratio changer.

FIG. 5B depicts a rear perspective view of the detachable and re-attachable conical area ratio changer.

Figure 1A:
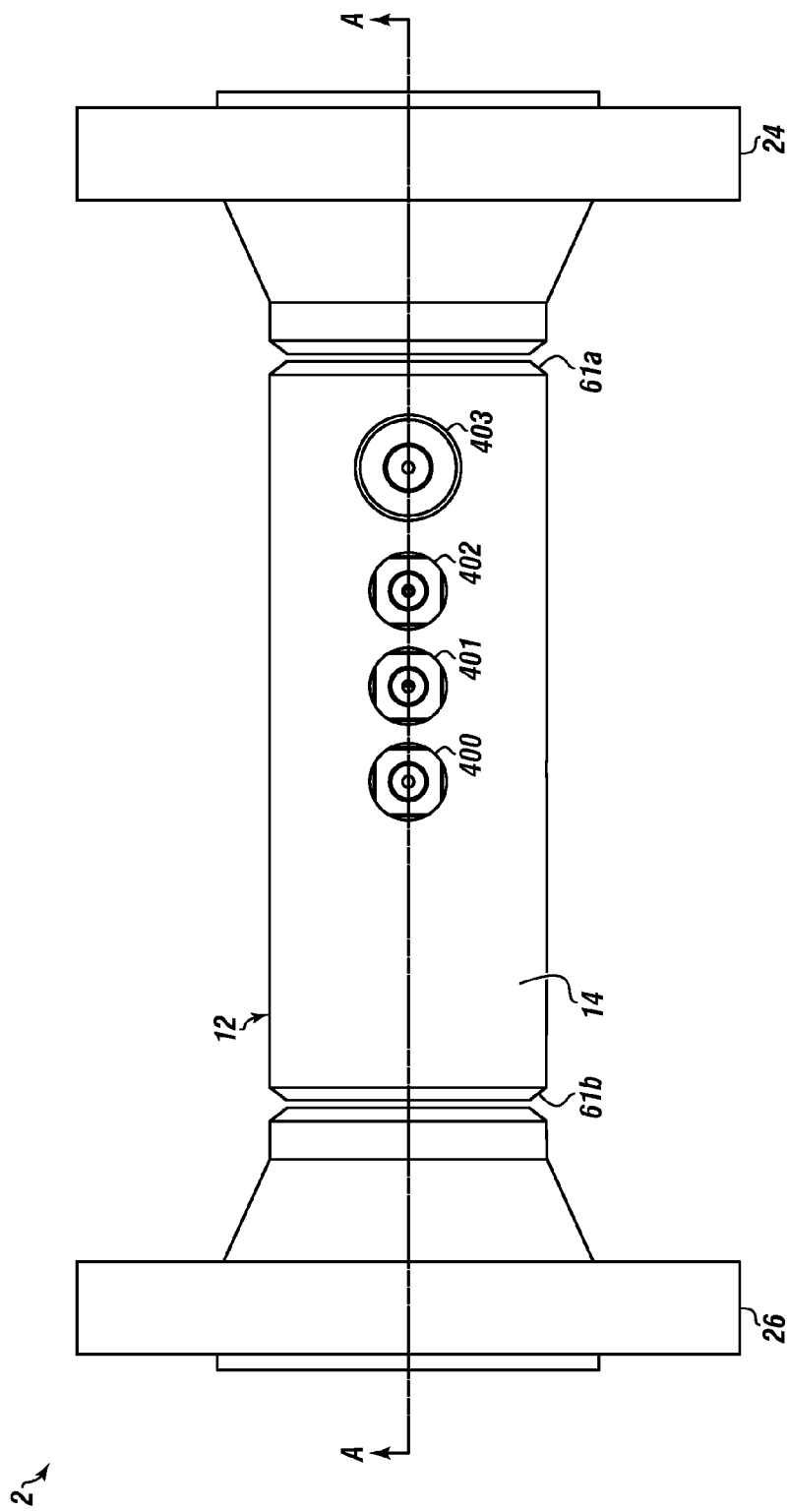
FIG. 1A depicts a perspective view of the self-calibrating fluid measuring device.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The current embodiments generally relate to a self-calibrating fluid measuring device for calculating density and velocity of a fluid.

The self-calibrating fluid measuring device can have a hollow body with a chamber for receiving and emitting a fluid. The self-calibrating fluid measuring device can further have a ledge and a conical section mount concentrically positioned in the hollow body secured to the ledge.

The self-calibrating fluid measuring device can have a plurality of sensors, which can be mounted in a plurality of ports, which can further extend into the chamber.

In embodiments, the hollow body can be substantially cylindrical.

The conical section mount can be machine centered into the chamber. The conical section mount can have a bore, which can be machined centrally through the conical section mount.

A detachable and re-attachable conical area ratio changer can be connected to the conical section mount. The detachable and re-attachable conical area ratio changer can have a central bore and a hollow fastener, which can be configured to align and center the detachable and re-attachable conical area ratio changer to the conical section mount during measuring.

In embodiments, the detachable and re-attachable conical area ratio changer can be variable in size, such as, to be larger or smaller in size to accommodate greater or smaller fluid volumes through the hollow body.

A benefit of the self-calibrating fluid measuring device is that is designed to determine fluid flowing density and fluid volume continuously in one body.

A benefit of the self-calibrating fluid measuring device is that it is self-calibrating to correct and determine the flow density.

A benefit of the self-calibrating fluid measuring device is that is has no moving parts, which lengthens its life.

A benefit of the self-calibrating fluid measuring device is that when it installed the self-calibrating fluid measuring device is self-centering.

A benefit of the self-calibrating fluid measuring device is that there is no welding required in the interior components of the fluid measuring device, which reduces metal deformity and generates machined high accuracy.

The self-calibrating fluid measuring device can be made from different metals and metal thickness as well as different sizes to accommodate different corrosive fluids and higher volumes, which allows for higher pressure for downhole fluid measuring and metering.

The self-calibrating fluid measuring device can be self-adapting to changing flow by means of changing the detachable and re-attachable conical area ratio changer (ARC).

In embodiments, components of the self-calibrating fluid measuring device can be easily and quickly changed due to wear and tear without the need to change the entire fluid measuring device.

A feature of the embodiments is that the self-calibrating fluid measuring device can accommodate high velocity fluid flow with this fluid measuring device to allow a low and high Reynolds number, wherein the flow can be as low as 100 lb/hr to millions of pounds per hour.

The embodiments can allow the producer to know the level of the saturation steam, which is very effective in oil production. Not knowing the level of steam saturation can lead to dumping water instead of steam in the well, which causes lower oil production and lack of efficiency.

Specific structural and functional details disclosed herein are not to be interpreted as limiting, but merely as a basis of the claims and as a representative basis for teaching persons having ordinary skill in the art to variously employ the present invention and embodiments.

Turning now to the Figures, FIG. 1A depicts a perspective view of the self-calibrating fluid measuring device.

The self-calibrating fluid measuring device 2 can have a hollow body 12 for receiving and emitting a fluid.

The self-calibrating fluid measuring device 2 can calculate density and velocity of the fluid flowing through the hollow body 12.

The hollow body 12 is shown with an exterior surface 14. A first beveled surface 61a can be on at least one end of the hollow body 12. The first beveled surface 61a can be configured to connect in line with an upstream conduit 24.

A second beveled surface 61b can be on at least one end of the hollow body, shown on the opposite end of the hollow body 12. The second beveled surface 61b can be configured to connect in line with a downstream conduit 26.

In embodiments, the self-calibrating fluid measuring device can have a plurality of tabs 400, 401, 402, and 403. In this embodiment, a temperature tab 400 can be mounted in a temperature port, a downstream pressure tab 401 can be mounted in a downstream pressure port, a ram velocity tab 402 can be mounted in a ram velocity port, and an upstream pressure tab 403 can be mounted in a static upstream pressure port.

In embodiments, each tab of the plurality of tabs can secure to and center a sensor in a port.

Figure 1B:
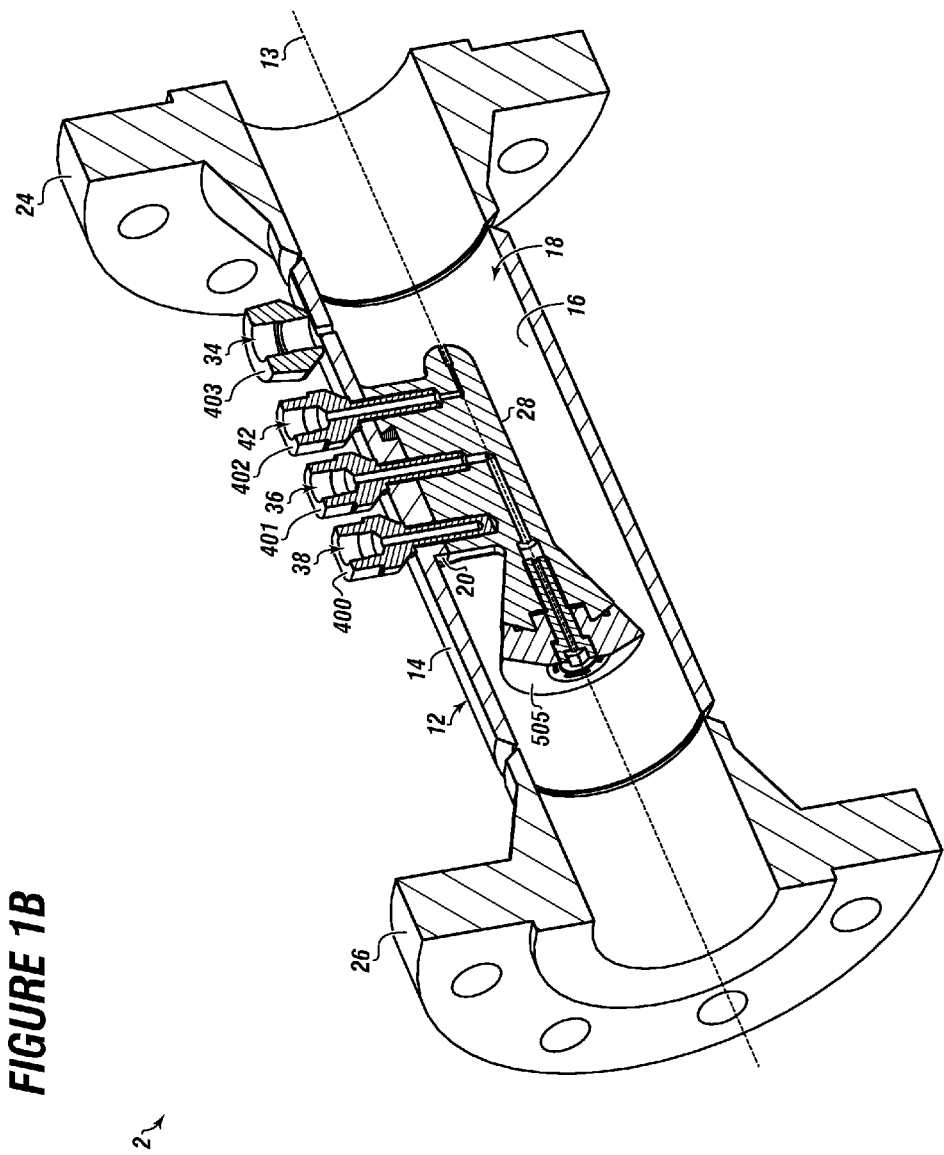
FIG. 1B is a cross sectional view of the self-calibrating fluid measuring device of FIG. 1A.

FIG. 1B is a cross sectional view of the self-calibrating fluid measuring device of FIG. 1A.

The self-calibrating fluid measuring device 2 can have a longitudinal axis 13 and a chamber 18.

The hollow body 12 is shown with an interior surface 16 and the exterior surface 14, which can be positioned between the upstream conduit 24 and the downstream conduit 26.

A ledge 20 can be carved from or connected to the interior surface 16 of the hollow body 12.

A conical section mount 28 can be mounted to the ledge 20. In embodiments, the conical section mount 28 can be position in the hollow body 12.

In embodiments, the conical section mount 28 can be concentrically disposed within the hollow body 12.

A detachable and re-attachable conical area ratio changer 505 can be connected to the conical section mount 28.

In embodiments, the self-calibrating fluid measuring device can have plurality of ports 38, 36, 42 and 34. In this embodiment, a temperature port 38, a downstream pressure port 36, a ram velocity port 42, and a static upstream pressure port 34 are shown.

In embodiments, the plurality of ports 38, 36, 42 and 34 can be drilled through the hollow body 12, wherein the plurality of ports can be aligned with each other.

In this embodiments, the plurality of tabs 400, 401, 402, and 403 are shown inserted into each port of the plurality of ports 38, 36, 42, and 34, such as, the temperature tab 400 can be mounted in the temperature port 38, the downstream pressure tab 401 can be mounted in the downstream pressure port 36, the ram velocity tab 402 can be mounted in the ram velocity port 42, and the upstream pressure tab 403 can be mounted in the static upstream pressure port 34.

In embodiments, the plurality of tabs and the plurality of ports can be used to support sensors and can enable the sensors to sense fluid through each port of the plurality of ports.

FIG. 1C is an assembled view of the self-calibrating fluid measuring device of FIG. 1A.

The self-calibrating fluid measuring device 2 is shown with the hollow body 12 having the exterior surface 14, which can be located between the upstream conduit 24 and the downstream conduit 26.

The plurality of tabs 400, 401, 402, and 403 can each have an angled surface 408a, 408b 408c, and 408d. Each angled surface 408a-408d can be positioned between a neck section and a head portion of each tab. In embodiments, each angled surface can support a weld. In embodiments, each weld can connect each tab to the hollow body. In embodiments, each weld can provide a fluid and pressure seal to ensure no movement of the conical section mount on the ledge, which can be a self-centering dovetail ledge.

In embodiments, threads can be formed on a shaft of each tab of the plurality of tabs to provide an additional fluid and pressure seal.

In this embodiment, a plurality of sensors 304, 302, 40, and 32 are shown mounted in the plurality of ports. In embodiments, the plurality of sensors can extend in to chamber.

A temperature sensor 304 can be mounted in the temperature port on the temperature tab 400. A cone downstream pressure sensor 302 can be mounted in the downstream pressure port on the downstream pressure tab 401. A ram velocity sensor 40 can be mounted in the ram velocity port on the ram velocity tab 402. An upstream static pressure sensor 32 can be mounted in the static upstream pressure port on the upstream pressure tab 403.

Figure 2A:
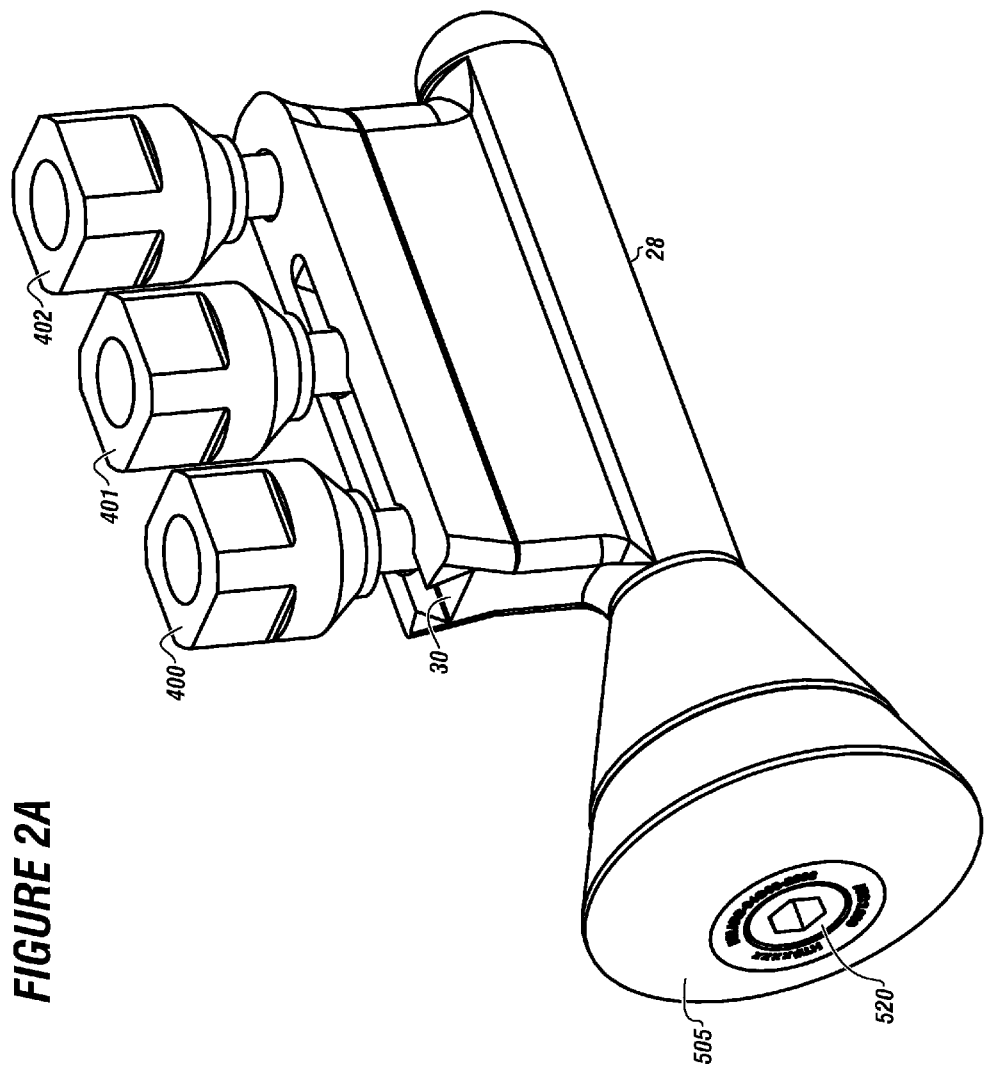
FIG. 2A depicts a perspective view of the conical section mount with the plurality of tabs.

FIG. 2A depicts a perspective view of the conical section mount with the plurality of tabs.

The plurality of tabs 400, 401, and 402 are shown mounted in the plurality of ports, wherein the each tab of the plurality of tabs and each port of the plurality of ports can extend into the conical section mount 28.

For example, the temperature sensor can mount to the temperature tab 400 and into the temperature port. In embodiments, the temperature tab 400 can be hollow with a closed end, wherein each of the other tabs can be hollow with an opened end. The temperature port and the temperature sensor can extend into the conical section mount 28.

For example, the downstream pressure tab 401 is shown mounted in the downstream pressure port. The downstream pressure tab 401 and the downstream pressure port can extend into the conical section mount 28 downstream from a static upstream pressure port.

For example, the ram velocity sensor can be mounted in the ram velocity port using the ram velocity tab 402. The ram velocity tab can extend upstream into the fluid flow opposite the direction of the fluid flow through the hollow body. The ram velocity tab can be mounted in the ram velocity port and can penetrate to the interior surface of the hollow body and can further extend into the conical section mount 28.

The conical section mount 28 can have a mounting surface 30 for engaging the ledge of the hollow body.

The detachable and re-attachable conical area ratio changer 505 can be connected to the conical section mount 28 and a hollow fastener 520 is also shown.

Figure 2B:
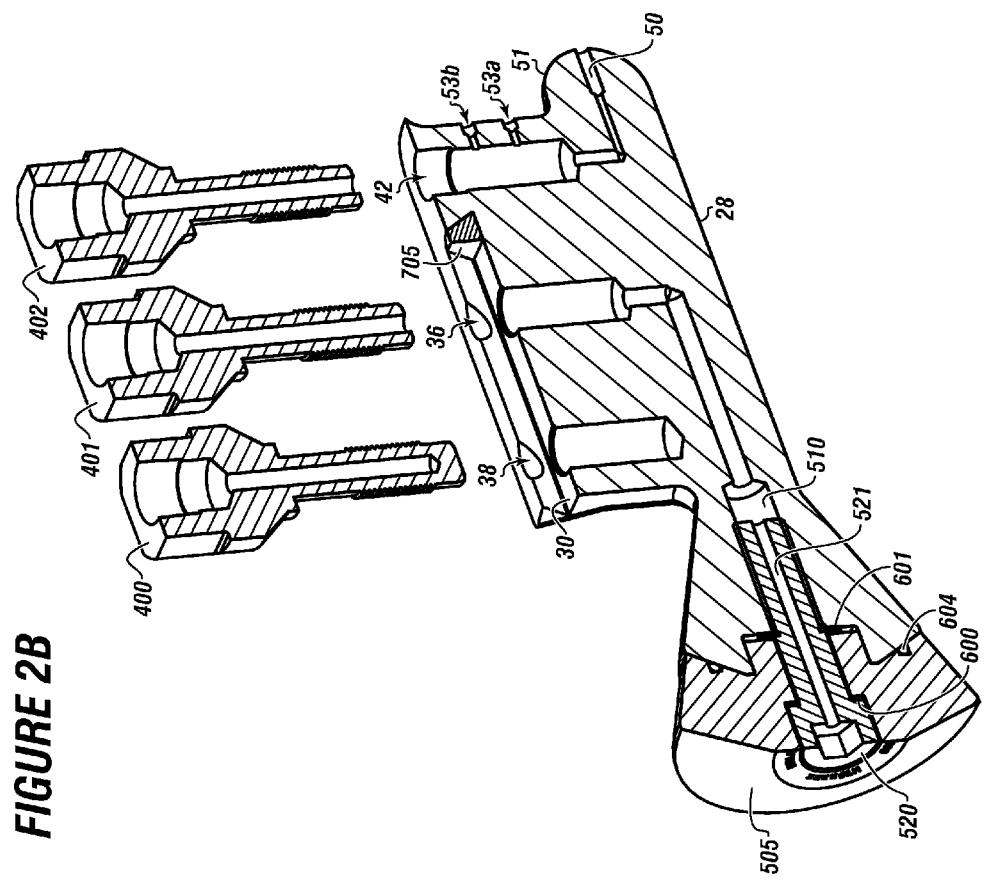
FIG. 2B shows a cross sectional view of the conical section mount of FIG. 2A.

FIG. 2B shows a cross sectional view of the conical section mount of FIG. 2A.

A ram inlet bore 50 can be located in the conical section mount 28, wherein the ram inlet bore can be fluidly communication or engagement with the ram velocity port 42 to receive fluid pressure created by the velocity from a direction of fluid flow.

The ram inlet bore 50 can be substantially parallel to the fluid flow through the hollow body and the ram velocity port 42 can be substantially perpendicular to the ram inlet bore 50.

The ram inlet bore 50 can penetrate to the interior surface of the hollow body.

The conical mount section 28 can have a protruding dome 51, wherein the protruding dome 51 can be centrally extending into the fluid flow upstream of the conical section mount 28.

The protruding dome 51 can be configured to enable fluid velocity to be captured without the influence of the conical section mount, which can reduce fluid velocity.

With this device, a processor can be connected to the self-calibrating fluid measuring device, which can allow a user or an operator to solve for density of the fluid entering the hollow body. For example, the processor can use Bernoulli's equation to solve for fluid density, which can enable fast and continuous determination of fluid density for multiple samples passing through the self-calibrating fluid measuring device sequentially and continuously. This computation can be achieved by combining the upstream velocity with the downstream pressure of the flowing fluid using the multiple sensors and then computing the flowing density using Bernoulli's equation.

In embodiments, the conical section mount 28 can be machine centered into the chamber to the ledge with a stop 705. The stop 705 can hold the conical section mount 28 to the ledge at a predetermined location in the hollow body.

A bore 510 can be used to assist in aligning and centering the detachable and re-attachable conical area ration changer 505 to the conical section mount 28, which can be through a horizontal section of the self-calibrating fluid measuring device. The bore 510 can fluidly communicate with the downstream pressure port 36.

The hollow fastener 520 can have a hollow fastener bore 521, which can be fluidly connected though the bore 510. The hollow fastener 520 can align and center the detachable and re-attachable conical area ratio changer 505 to the conical section mount 28.

The detachable and re-attachable conical area ratio changer 505 is shown as a frustoconical annular disc with the bore 510 disposed there through.

A seal 604 can be disposed between the detachable and re-attachable conical area ratio changer 505 and the conical section mount 28.

A lock washer 600 can secure the hollow fastener 520 to the detachable and re-attachable conical area ratio changer 505.

A retainer ring 601 can assist in holding the detachable and re-attachable conical area ratio changer 505 to the hollow fastener 520.

In embodiments, a plurality of ram velocity ports 53a and 53b can be fluidly connecting to the ram inlet bore 50 and the ram velocity port 42 simultaneously.

The plurality of ram velocity ports 53a and 53b can be perpendicular to fluid flow in the hollow body and parallel to fluid flow into the ram inlet bore 50.

The plurality of tabs 400, 401 and 402 are shown detached from the plurality of ports 38, 36 and 42. Shown here as the temperature tab 400, the downstream pressure tab 401, and the ram velocity tab 402.

The mounting surface 30 can enable the ledge to secure with the conical section mount, which can also create a flush mount between the ledge and the conical section mount 28.

In embodiments, the self-calibrating fluid measuring device can have additional ports for monitoring additional physical properties and are not limited to only the ports described herein.

FIG. 3A is a cross sectional view of the hollow body of the self-calibrating fluid measuring device.

The hollow body is shown with the exterior surface 14 and the interior surface 16.

The ledge 20 can be mounted to the interior surface 16 of the hollow body 12.

FIG. 3B is a view of the hollow body along the cut lines B-B shown in FIG. 3A.

The hollow body 12 is shown having a first diameter 19, the chamber 18, the first beveled surface 61a, the second beveled surface 61b, the exterior surface 14, the interior surface 16 and the ledge 20.

In embodiments, the ledge can be a self-centering dovetail ledge. In embodiments, the ledge can be carved from a solid metal pipe or an extra thick pipe for high pressure applications.

The plurality of ports 38, 36, 42, and 34 are shown as the temperature port 38, the downstream pressure port 36, the ram velocity port 42 and the static upstream pressure port 34.

In embodiments, the static upstream pressure port can be disposed through a sensor mount and can penetrate to the interior surface of the hollow body enabling sensing and recording of high pressure at the interior surface of the hollow body upstream from the conical section mount.

FIG. 4 is a perspective view of a tab of the plurality of tabs with a bore for receiving a sensor usable in the hollow body.

A tab 400 of the plurality of tabs can have a head portion 429, a tab bore 427 for receiving a sensor formed through the head portion 429, a shaft portion 433, threads 435 formed on the shaft portion 433, a neck section 431 connected between the shaft portion 433 and the head portion 429, and an angled surface 408 between the neck section and the head portion. The angled surface 408 can support a weld connecting the tab to exterior surface of the hollow body.

Each tab can have from two to four faces for assisting in positioning each tab in the hollow body. The faces 425 can be used to provide a mechanism to allow make-up with a sensor. The faces 425 can allow each tab to be torqued through the external surface of the hollow body.

FIG. 5A depicts a front perspective view of the detachable and re-attachable conical area ratio changer.

In operation, the detachable and re-attachable conical area ration changer 505 can have a central bore 506, which can receive the hollow fastener, which can form a flush fit securing the detachable and re-attachable conical area ratio changer 505 onto the conical section mount.

In embodiments, the detachable and re-attachable conical area ratio changer 505 can terminate in a flat surface 746. The surface 746 can be formed parallel to the interior surface of the hollow body to reduce wear of the detachable and re-attachable conical area ratio changer 505 and promote unhindered fluid flow.

In embodiments, the flat surface 746 can be machined to maintain concentricity of the detachable and re-attachable conical area ratio changer 505 with respect to the interior surface of the hollow body.

In embodiments, an axial dimension of the flat surface 746 can be optimized as a function of flow range, including operating conditions.

Due to the flat configuration of the flat surface 746, wear on the detachable and re-attachable conical area ratio changer 505 can be reduced, thereby maintaining the accuracy of the data acquired.

The detachable and re-attachable conical area ratio changer can also have a flat face 748 and a diameter passage 1200, which can engage a head of the hollow fastener.

The detachable and re-attachable conical area ratio changer 505 can have a beveled face 744 that can match a sloped surface of the conical section mount to provide obstruction to a flow stabilizer.

FIG. 5B depicts a rear perspective view of the detachable and re-attachable conical area ratio changer.

The detachable and re-attachable conical area ratio changer 505 is shown with the flat surface 746 and the beveled face 744.

The detachable and re-attachable conical area ratio changer 505 can have a plurality of mating surfaces, such as a first mating surface 1113, a second mating surface 1114, a third mating surface 742, and a fourth mating surface 1116.

In embodiments, at least one mating surface, or as shown here, the second mating surface 1114 can correspond to the mounting surface of the conical section mount, which can allow for self-aligned and self-centered installment of the detachable and re-attachable conical area ratio changer 505. The second mating surface 1114 and the mounting surface of the conical section mount can be formed with tight tolerances to maintain concentric consistency.

The detachable and re-attachable conical area ratio changer 505 can have a second diameter passage 1220 for engaging the hollow fastener.

Figure 6:
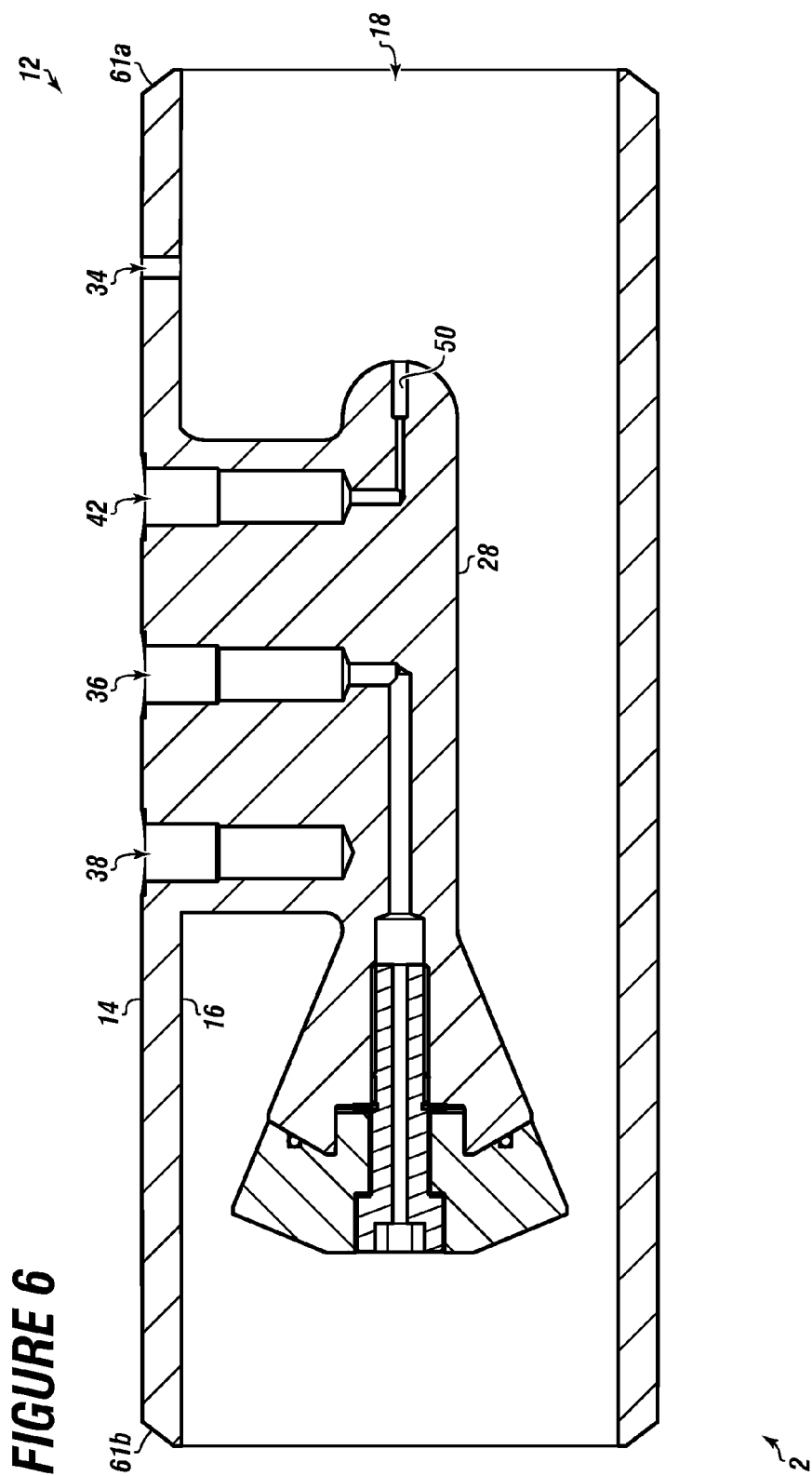
FIG. 6 shows another embodiment of the self-calibrating fluid measuring device.

FIG. 6 shows another embodiment of the self-calibrating fluid measuring device.

The self-calibrating fluid measuring device 2 can have the hollow body 12 with the exterior surface 14, the interior surface 16, the first beveled surface 61a, the second beveled surface 61b and the chamber 18.

In this embodiment, the conical section mount 28 can be formed as a single piece unit. In embodiments, the single piece unit can be made of cast metal.

The plurality of ports 38, 36, 42, 34 are shown as the temperature port 38, the downstream pressure port 36, the ram velocity port 42, and the static upstream pressure port 34.

In embodiments, the ram inlet bore 50 can fluidly engage the ram velocity port 42 to receive pressure generated by fluid impacting the ram inlet bore.

The self-calibrating fluid measuring device can have multiple elements, meters, and sensors in one body that can allow for solving for fluid density of the fluids being measured.

In embodiments, the self-calibrating fluid measuring device can range in size from about ½ of an inch and up, such as about 48 inches or larger, depending on flow serviced.

The wall thickness, such as of the hollow body, the chamber, the self-calibrating fluid measuring device, or combinations thereof, can be a thickness that can accommodate from standard low pressure to extremely high pressure in excess of 20,000 psi for high pressure production wells.

This embodiment evades issues relating to well sanding resulting in the complete damage to oil wells from drying up from oil and just water or gas production.

The self-calibrating fluid measuring device can enable an operator to know the saturation level steam during well injection to improve oil production.

The components of the self-calibrating fluid measuring device can be made from carbon steel, alloy steels, stainless steel, metal alloys, such as HASTELLORY®, metal alloys containing nickel and copper, such as MONEL®, or other materials as required to prevent attack by the fluid being passed through the self-calibrating fluid measuring device.

In embodiments, the self-calibrating fluid measuring device can have a hollow body that can be manufactured in different thicknesses and sizes, for example 0.5 inches to 48 inches, to meet required flow capacity and pressure rating, for example 1 psi to 15,000 psig.

In embodiments, the hollow body and conical section mount can be made to interference fit tolerances, which can allow a press fit between the two components to ensure concentricity and alignment within the hollow body.

In embodiments, the components can be press fitted together, such as by hydraulic pressing. In embodiments, the components can be heated and cooled in combination to allow mating of parts.

While these embodiments have been described with emphasis on the embodiments, it should be understood that within the scope of the appended claims, the embodiments might be practiced other than as specifically described herein.

What is claimed is:

1. A self-calibrating fluid measuring device for calculating density and velocity of a fluid comprising:
   a. a hollow body for receiving and emitting the fluid, the hollow body comprising:
      an exterior surface, an interior surface, and a chamber;
   b. a ledge formed from the interior surface of the hollow body;
   c. a conical section mount, wherein the conical section mount is concentrically disposed within the hollow body and secured to the ledge, and further wherein the conical section mount comprises a mounting surface to create a flush mount with the ledge;
   d. an upstream static pressure sensor mounted in a static upstream pressure port, the upstream static pressure sensor extending into the chamber;
   e. a cone downstream pressure sensor mounted in a downstream pressure port, the downstream pressure port extending into the conical section mount downstream from the static upstream pressure port;
   f. a temperature sensor extending into a temperature port, wherein both the temperature sensor and the temperature port extend into the conical section mount;
   g. a ram velocity sensor mounted in a ram velocity port, the ram velocity port extending into the chamber proximate an upstream end of the hollow body;
   h. a ram inlet bore fluidly engaging the ram velocity port to receive pressure generated by the fluid impacting the ram inlet bore;
   i. a detachable and re-attachable conical area ratio changer connected the conical section mount, wherein the detachable and re-attachable conical area ratio changer comprises a central bore fluidly communicating with the downstream pressure port;
   j. a bore in the conical section mount; and
   k. a hollow fastener with a hollow fastener bore fluidly connected to the bore, wherein the hollow fastener aligns and centers the detachable and re-attachable conical area ratio changer to the conical section mount.

2. The self-calibrating fluid measuring device of claim 1, comprising a first beveled surface at a first end of the hollow body configured to connect in line with an upstream conduit and a second beveled surface at a second end of the hollow body configured to connect in line with a downstream conduit.

3. The self-calibrating fluid measuring device of claim 1, wherein the hollow body is substantially cylindrical, and wherein the conical section mount is machine centered into the chamber, and wherein the bore is machine centered through the conical section mount.

4. The self-calibrating fluid measuring device of claim 1, comprising additional ports for monitoring mass, viscosity, and other fluid measuring devices.

5. The self-calibrating fluid measuring device of claim 1, wherein the static upstream pressure port is disposed through the conical section mount and penetrates the interior surface of the hollow body enabling static pressure sensing and recording of upstream pressure at the interior surface of the hollow body upstream from the conical section mount.

6. The self-calibrating fluid measuring device of claim 1, wherein the detachable and re-attachable conical area ratio changer is a substantially frustoconical annular disc comprising a flat surface to reduce wear of the detachable and re-attachable conical area ratio changer and promote unhindered fluid flow.

7. The self-calibrating fluid measuring device of claim 1, wherein the detachable and re-attachable conical area ratio changer is variable in size to be larger or smaller, to accommodate variable for fluid flow while maintaining accuracy, a volume of fluid flow increasing or decreasing caused by the size of the conical section mount.

8. The self-calibrating fluid measuring device of claim 1, wherein the hollow body and the conical section mount are a single piece unit of cast metal.

9. The self-calibrating fluid measuring device of claim 1, wherein the conical section mount is centered into the chamber to the ledge with a stop, wherein the stop holds the conical section mount to the ledge at a predetermined location in the hollow body.

10. The self-calibrating fluid measuring device of claim 1, wherein the conical mount section has a protruding dome centrally extending into the fluid flow upstream of the conical section mount, the protruding dome configured to enable fluid velocity to be captured without the influence of the conical section mount.

11. The self-calibrating fluid measuring device of claim 1, wherein the ledge is a self-centering dovetail ledge.

12. The self-calibrating fluid measuring device of claim 1, comprising a plurality of ram velocity ports connecting to the ram inlet bore and the ram velocity port, wherein the plurality of ram velocity ports are perpendicular to the fluid flow in the hollow body and parallel to the ram inlet bore.

13. The self-calibrating fluid measuring device of claim 1, comprising a plurality of tabs, wherein each tab of the plurality of tabs is mounted in at least one port, wherein the plurality of tabs comprise a temperature tab mounted in the temperature port, a downstream pressure tab mounted in the downstream pressure port, a ram velocity tab mounted in the ram velocity port, an upstream pressure tab mounted in the static upstream pressure port, and further wherein each tab of the plurality of tabs secures to and centers at least one sensor in the at least one port.

14. The self-calibrating fluid measuring device of claim 13, wherein each tab of the plurality of tabs has a head portion with a tab bore for receiving the at least one sensor formed through the head portion, a shaft portion, threads formed on the shaft portion, a neck section connected between the shaft portion and the head portion, and an angled surface between the neck section and the head portion, the angled surface for supporting a weld connecting each tab of the plurality of tabs to the hollow body.

15. The self-calibrating fluid measuring device of claim 1, further comprising a lock washer securing the hollow fastener to the detachable and re-attachable conical area ratio changer and a retainer ring to hold the detachable and re-attachable conical area ratio changer.

16. The self-calibrating fluid measuring device of claim 15, further comprising a seal disposed between the detachable and re-attachable conical area ratio changer and the conical section mount.

17. The self-calibrating fluid measuring device of claim 1, wherein the detachable and re-attachable conical area ratio changer comprising: a front side with the central bore disposed there through, wherein the central bore is configured to receive the hollow fastener, a flat surface that can be disposed parallel to the interior surface to reduce wear of the detachable and re-attachable conical area ratio changer and promote unhindered fluid flow, and a flat face.

18. The self-calibrating fluid measuring device of claim 17, wherein the detachable and re-attachable conical area ratio changer further comprising: a back side with the central bore, a beveled face that can match a sloped surface of the conical section mount, a first mating surface, a second mating surface, a third mating surface, and a fourth mating surface, wherein the second mating surface corresponds to the mounting surface of the conical section mount, allowing for self-aligned and self-centered installment of the detachable and re-attachable conical area ratio changer, and the second mating surface and the mounting surface of the conical section mount can be formed with tight tolerances to maintain concentric consistency.

\* \* \* \* \*